(12) United States Patent
McGinnis et al.

(10) Patent No.: US 7,727,559 B2
(45) Date of Patent: Jun. 1, 2010

(54) INHIBITION OF REACTIVE OXYGEN SPECIES AND PROTECTION OF MAMMALIAN CELLS

(75) Inventors: James F. McGinnis, Edmond, OK (US); Junping Chen, Oklahoma City, OK (US); Lily Wong, Oklahoma City, OK (US); Steve Sezate, Oklahoma City, OK (US); Sudipta Seal, Oviedo, FL (US); Swanand Patil, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days.

(21) Appl. No.: 11/412,665

(22) Filed: Apr. 27, 2006

(65) Prior Publication Data

US 2006/0246152 A1 Nov. 2, 2006

Related U.S. Application Data

(62) Division of application No. 11/412,665, filed on Apr. 27, 2006.

(60) Provisional application No. 60/676,043, filed on Apr. 29, 2005, provisional application No. 60/716,630, filed on Sep. 13, 2005.

(51) Int. Cl.
*A61K 33/24* (2006.01)
*A01N 59/16* (2006.01)

(52) U.S. Cl. ........................................ 424/617; 424/489

(58) Field of Classification Search .................. 424/401, 424/421, 427, 429
See application file for complete search history.

(56) References Cited

U.S. PATENT DOCUMENTS

| 2003/0187077 A1* | 10/2003 | Chane-Ching | ............... 516/31 |
| 2004/0241206 A1* | 12/2004 | Ketelson et al. | ............... 424/429 |
| 2006/0150526 A1* | 7/2006 | Ota et al. | ............... 51/307 |

OTHER PUBLICATIONS

Ming-Shyong Tsai, The Study of the synthesis of nano-grade cerium oxide powder, Materials Letters, 58, 2270-2274, 2004.*
Sigma_Aldrich Hand Book (2002004, p. 400).*
P. Moongkarndi, K. Nuttavut, S. Kalungka, O. Luanratana, N. Pongpan, N. Neungton, "Antiproliferation, antioxidation and induction of apoptosis by *Garcinia mangostana* (mangosteen) on SKBR3 human breast cancer cell line", Journal of Ethno-Pharmacology, vol. 90, (2004) pp. 161-166.

T.H. Margrain, M. Boulton, J.Marshall, D.H. Sliney, "Do blue light filters confer protection against age-related macualar degeneration?", Progress in Retinal and Eye Research, vol. 23 (2004), pp. 523-531.
D. Bailey, L. Chow, S. Merchant, S.C. Kuiry, S. Patil, S. Seal, and B. Rzigalinski, "Cerium Oxide Nanoparticles Extend Cell Longevity and Act as Free Radical Scavengers", online, [retrieved on Apr. 24, 2006] Retrieved from: http://www.med.miami.edu.mnbws/Rzigalinksill,.html.
Rzigalinski, Beverly Ann, et al., "Cerium oxide nanoparticles increase the lifespan of cultured brain cells and protect against free radical and mechanical trauma" FASEB Journal, vol. 17 No. 4-5 (Mar. 2003), Page Abstract No. 377.24 URL, XP008095016 & FASEB Meeting on Experimental Biology: Translating the Genome, San Diego, CA, USA, Apr. 11-15, 2003 ISSN: 0892-6638 *Abstract*.
Cook, et al., "Neuronal Damage Induced by Polychlorinated Biphenyls is Partically Reversed by Cerium Oxide Nanoparticles"[online] vol. 2003, 2003, XP008095032 Retreived from the Internet: URL:http://sfn.scholarone.com/itin2003/main/htm]?new_page_id=126&abstract_id=14513&p_num=669.13& is_tech=0> [retrieved on Aug. 5, 2008} *abstract*.
Tusnekawa, S., et al., "Lattice relaxation of monosize Ce02-x nanocrystalline particles" Applied Surface Science Elsevier Netherlands, vol. 152, No. 1-2, Nov. 1999, pp. 53-56, XP002491212 ISSN: 0169-4332 * p. 53, col. 1, paragraph 2- col. 2, parahraph 1 *.
Hooper, Claire, Y., et al., "New treatment in age-related macular degeneration" Clinical & Experimental Ophthalmology, Oct. 2003, pp. 376-391, XP002491214 ISSN: 1442-6404 * pp. 378-382*.

* cited by examiner

*Primary Examiner*—Michael G Hartley
*Assistant Examiner*—Jagadishwar R Samala
(74) *Attorney, Agent, or Firm*—Brian S. Steinberger; Joyce P. Morlin; Law Offices of Brian S. Steinberger, P.A.

(57) ABSTRACT

Methods and compositions useful for neuronal protection in retinal cells in vitro and the protection of mammalian cells from reactive oxygen species in vivo are provided. Ultrafine nano-size cerium oxide particles, less than 10 nanometers in diameter, have been provided to decrease reactive oxygen species (ROS) in retina tissue that generates large amounts of ROS. These reactive oxygen species (ROS) are involved in light-induced retina degeneration and age-related macular degeneration (AMD). Cerium oxide nanoparticles have been used to promote the lifespan of retinal neurons and protect the neurons from apoptosis induced by hydrogen peroxide in vitro and in vivo. The neuronal protection in retinal cells is achieved by decreasing generation of intracellular reactive oxygen species (ROS). Thus, cerium oxide particles are used to promote the longevity of retinal neurons in vitro and mammalian cells in vivo.

2 Claims, 10 Drawing Sheets

Control

10nM CeO₂ + 100μM H₂O₂

Fig. 4F

20nM $CeO_2$ + 100μM $H_2O_2$

Fig. 4G

20nM $CeO_2$

INHIBITION OF REACTIVE OXYGEN SPECIES AND PROTECTION OF MAMMALIAN CELLS

This is a Divisional of application Ser. No.: 11/412,665 filed Apr. 27, 2006 which claims the benefit of priority to U.S. Provisional Patent Application No.: 60/676,043 filed Apr. 29, 2005 and claims benefit of U.S. Provisional Patent Application No.: 60/716,630 filed Sept. 13, 2005.

FIELD OF THE INVENTION

This invention relates to biological uses of nanoceria particles, and in particular to methods and compositions useful for neuronal protection in retinal cells in vitro and the protection of mammalian cells from reactive oxygen species in vivo and is supported in part by funding from the National Science Foundation and National Institutes of Health under the Contract numbers: P20 RR17703, FY014427, FY13050, and FY12190.

BACKGROUND AND PRIOR ART

Cerium is a silvery metallic element, belonging to the lanthanide group. Cerium Oxide ($CeO_2$) is used in precision polishing and lapping applications. Ultra fine nano-size cerium oxide, less than 10 nanometers, is more efficient for coating purposes. Recently, it was reported by B. Rzigalinski et al. that nanoparticles prolong the life of cortical neurons in culture 4 fold over the cells without treatment; decreased the intracellular Ca2+ concentration and prevented UV damage of cortical neurons. See B. Rzigalinski et al., "Cerium Oxide Nanoparticles Extend Cell Longevity and Act as Free Radical Scavengers" at website http://www.med.miami.edu/mnbws/Rzigalinski112.html. Based on its chemical characteristics, this effect is partially due to a decrease of reactive oxygen species (ROS).

Retina tissue generates a large amount of ROS which are involved in light-induced retina degeneration and age-related macular degeneration (AMD). The present invention tests the hypothesis that nanoparticles can promote the lifespan of retinal neurons in culture and protect them from apoptosis induced by hydrogen peroxide ($H_2O_2$) in vitro by decreasing the intracellular concentration of reactive oxygen species.

In 2004, T. H. Margrain et al. discuss the state of research in the treatment of age-related macular degeneration in *Progress in Retinal and Eye Research*, 2004, 23: 523-531, "Do Blue Light Filters Confer Protection Against Age-Related Macular Degeneration?" The problem of apoptosis in the body is discussed in an article by P. Moongkarndi et al. in "Antiproliferation, Antioxidation and Induction of Apoptosis by Garcinia Mangostana (Mangosteen) on SKBR3 Human Breast Cancer Cell Line", *Jl. of Ethnopharmacology*, 2004, 90: 161-166.

Often persons suffering from light-induced retina degeneration and age-related macular degeneration (AMD) are without satisfactory remedies to prevent the eventual outcome of blindness. There are some proteins available for neuronal protection of retinal cells, however, they are big molecules and over time their effect may fade away.

It is desirable to find reliable solutions to prolong the lifespan of retinal neurons so that blindness is avoided for persons with retina degeneration and AMD.

In addition to diseases of the eye, many human diseases are due to the death of cells in specific tissues or organs. The majority of those diseases are due to accumulation of metabolic insults from reactive oxygen species originating within or outside of the cells. These diseases include all forms of blindness whether hereditary, light-induced, or physical damage such as occurs in retinal detachment. In addition, damage due to ageing, stroke, cardiac infarction, burns, etc, which proceed through reactive oxygen species, can be addressed with the nanoceria particles of the present invention.

The present invention promotes a longer lifespan for retinal neurons. The greatest benefit of the nanoceria is its ability to get inside the cells and provide protection from reactive oxygen species (ROS); other body systems and tissues can also be protected from damage due to ROS.

SUMMARY OF THE INVENTION

A primary objective of the present invention is to promote the lifespan of retinal neurons in culture.

A secondary objective of the present invention is to protect retinal neurons from apoptosis induced by hydrogen peroxide ($H_2O_2$) in vitro.

A third objective of the present invention is to protect retinal neurons from apoptosis induced by reactive oxygen species in vivo.

A fourth objective of the present invention is to inhibit the rise in the intracellular concentration of reactive oxygen species (ROS).

A fifth objective of the present invention is to provide method for inhibiting apoptosis induced by $H_2O_2$ of retinal neurons in vitro in a dose and time dependent manner.

A sixth objective of the present invention is to provide method for inhibiting apoptosis induced by reactive oxygen species in retinal neurons in vivo in a dose and time dependent manner.

A seventh objective of the present invention is to provide a method for preventing an increase in the intracellular reactive oxygen species (ROS) in a dose and time dependent manner.

An eighth objective of the present invention is to manufacture and modify cerium oxide ($CeO_2$) nanoparticles for effective use in neuronal protection in retinal cells.

A ninth objective of the present invention is to manufacture and modify cerium oxide ($CeO_2$) nanoparticles for effective use in mammalian cells in vivo to inhibit damage caused by reactive oxygen species (ROS).

A preferred composition for promoting longevity of retinal neurons includes at least one of $CeO_{n1}$ wherein $0<n1<2$, and $0<n2<3$ in the form of ultra-fine particles. The preferred ultra-fine particles have a diameter in a range between approximately 1 nanometer (nm) and approximately 10 nm and the preferred $CeO_{n1}$ is further defined as n1 equals approximately 2.

A preferred composition for inhibiting apoptosis induced by hydrogen peroxide oxidation of retinal neurons includes at least one of $CeO_{n1}$ wherein $0<n1<2$, and $0<n2<3$ in the form of ultra-fine particles. The preferred ultra-fine particles have a diameter in a range between approximately 1 nanometer (nm) and approximately 10 nm and the preferred $CeO_{n1}$ is further defined as n1 equals approximately 2.

A preferred composition for inhibiting apoptosis of retinal neurons in a dose and time dependent manner includes at least one of $CeO_{n1}$ wherein $0<n1<2$, and $0<n2<3$ in the form of ultra-fine particles. The preferred ultra-fine particles have a diameter in a range between approximately 1 nanometer (nm) and approximately 10 nm and the preferred $CeO_{n1}$ is further defined as n1 equals approximately 2.

A more preferred composition that decreases the concentration of intracellular reactive oxygen species (ROS) includes at least one of $CeO_{n1}$ wherein $0<n1<2$, and $0<n2<3$ in the form of ultra-fine particles. The more preferred composition is used in the treatment of diseases of the retina selected from the group consisting of light-induced retina degeneration and age-related macular degeneration, and is also used in vivo for the treatment of diseases in mammalian cells to inhibit damage caused by reactive oxygen species (ROS).

The mammalian cells that can be treated by the composition of the present invention, include, but are not limited to, retinal neurons, brain cells, heart cells, skin cells, liver cells, kidney cells and peripheral nervous system cells.

A preferred method for promoting longevity of retinal neurons includes preparing ultra-fine particles of at least one of $CeO_{n1}$ wherein $0<n1<2$, and $0<n2<3$ in a preselected concentration, and adding the preselected concentration of $CeO_{n1}$ wherein $0<n1<2$, and $0<n2<3$ to primary retinal neurons. The preferred ultra-fine particles have a diameter in a range between approximately 1 nanometer (nm) and approximately 10 nm and the $CeO_{n1}$ is further defined as n1 equals approximately 2. The preferred preselected concentrations of $CeO_2$ are in a range between approximately 3 nanomolar (nM) and approximately fifty nanomolar (nM), more preferably in a range between approximately 3 nanomolar (nM) and approximately twenty nanomolar (nM).

It is also preferred that the preselected concentrations of $CeO_2$ are added to primary retinal neurons in vitro and/or administered to mammalian cells in vivo to protect the mammalian body system from damage to any tissue due to reactive oxygen species (ROS).

Further objects and advantages of the present invention will be apparent from the following detailed description of a presently preferred embodiment which is illustrated schematically in the accompanying drawings.

DESCRIPTION OF THE PREFERRED EMBODIMENTS

Before explaining the disclosed embodiments of the present invention in detail it is to be understood that the invention is not limited in its application to the details of the particular arrangements shown since the invention is capable of other embodiments. Also, the terminology used herein is for the purpose of description and not of limitation.

The present invention has two embodiments describing in detail the in vitro and in vivo treatment of mammalian cells with ultra fine nano-size cerium oxide particles, less than 10 nanometers in diameter, to protect the "body system" from damage to any tissue due to reactive oxygen species (ROS).

Hydrogen peroxide ($H_2O_2$) is one of many reactive oxygen species. In the present invention, $H_2O_2$ is added directly to cultures for the in vitro treatments. $H_2O_2$ is not added to the live tissue samples, since $H_2O_2$ is one of the ROS products of light damage. The discussion below confirms that nanoceria particles inhibit all forms of reactive oxygen species (ROS).

For example, the nanoceria particles of the present invention can protect the brain against stroke and reperfusion injury, the heart cells from effects of cardiac infarction, the skin from UV rays and burn injuries. Neurodegeneration (e.g., Alzheimer's, Parkinson's, dementia, amyotrophic lateral sclerosis) and potentially mental retardation (due to loss of brain cells) within the central and peripheral nervous systems can also be inhibited. This protection can extend to diseases which produce chronic problems such as cirrhosis of the liver or kidney or the multi-organ effects of aging itself. The nanoceria can become the universal treatment for all major and minor diseases and events which involve reactive oxygen species.

The nanoceria ($CeO_2$ nanoparticles) have the ability to destroy toxic products of metabolism known as reactive oxygen species (ROS). It has been shown in one embodiment that the nanoceria particles prevent the ROS induced death of mammalian retinal neurons in culture (in vitro) and subsequently prolonged the life of the cells in culture and protected the cells from ROS. In the second embodiment, the ability to provide mammalian cell protection in vivo is disclosed.

The first embodiment of the present invention provides a method and composition for promoting the lifespan of retinal neurons and protecting the nerve cells in the eye from apoptosis induced by hydrogen peroxide ($H_2O_2$) in vitro by decreasing generation of intracellular reactive oxygen species. The treatment of the eye with ultra fine nano-size cerium oxide is a significant advance in biological uses of cerium oxide. Persons afflicted with such conditions as, light-induced retina degeneration and age-related macular degeneration (AMD) have hope for brighter, clearer vision.

The examples below provide further detail on the preparation and treatment of retinal nerve cells with $CeO_2$ nanoparticles.

EXAMPLE 1

Figure 1:
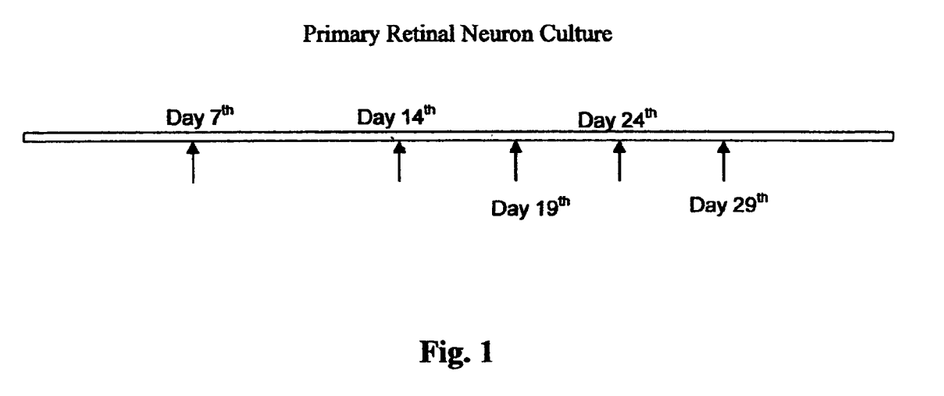
FIG. 1 is a timeline of exposure of a primary retinal neuron culture to treatment with cerium oxide nanoparticles.
Figure 2:
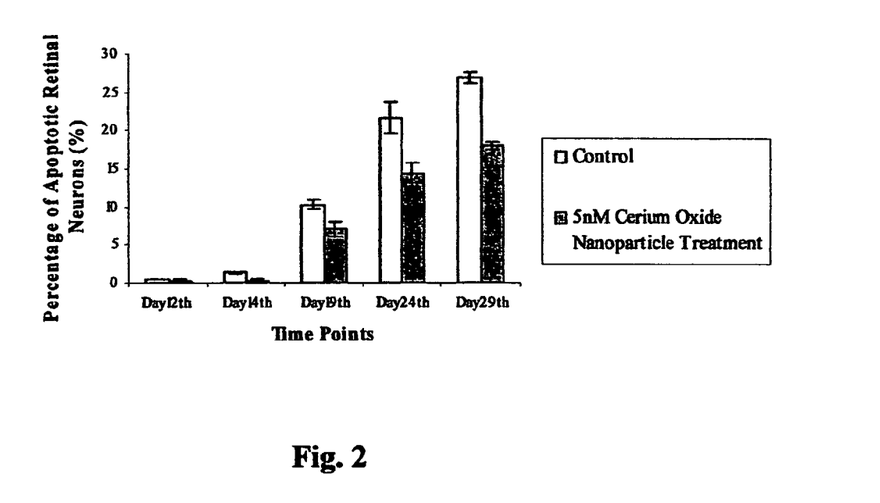
FIG. 2 is a graph showing the percentage of apoptotic retinal neurons in culture with and without 5 nanomoles (nM) cerium oxide nanoparticle treatment at different time points.

A primary retinal neuron culture is obtained from albino rat pups. Retinae of Sprague-Dawley albino rat pups (0-2-day old) were dissected out and mechanically dissociated in 25 ml of DMEM/F12 medium. After being filtered through 230 μm and 140 μm sieves, the dissociated cells were centrifuged at 1200 rpm for 5 min. The cell pellets were re-suspended in the medium to $1 \times 10^5$ cells/ml. 1 ml of the cell suspension was plated in each well pre-treated with 10 μg/ml of poly-D-lysine. The cells were maintained in the medium until day 7, when different concentrations of $CeO_2$ nanoparticles were added to the cultures. The timeline for the addition of $CeO_2$ nanoparticles is shown in FIG. 1. The treated neuronal cells were harvested on day 14, day 19, day 24 and day 29 after the beginning of treatment on day 7. The percentage of apoptotic retinal neurons in the culture with and without 5 nM $CeO_2$ nanoparticle treatment is shown in FIG. 2 at the $12^{th}$ day, $14^{th}$ day, 19 h day, $24^{th}$ day and $29^{th}$ day. Data are shown in M±S.D. Statistics were collected by Student t-test (n=3, *p<0.05, **p<0.01). FIG. 2 confirms that at every testing period the control with no $CeO_2$ nanoparticle treatment had a higher percentage of apoptotic retinal neurons in the culture, in contrast to the decreased percentage of apoptotic retinal neurons in the cells treated with 5 nM $CeO_2$ nanoparticles.

EXAMPLE 2

The detection of apoptosis by flow cytometry is illustrated in FIGS. 3, 4A-4H and 5. After periods of incubation with $CeO_2$ or $H_2O_2$, the cells were washed with serum free medium 3 times, followed by treatment of 1 ml of 1×trypsin for 2 min. After centrifuging, the cell pellet was resuspended in 500 μl of 1×PBS containing 5 μl of Annexin V-FITC and 25 μl of Propidium Iodide (PI). The kit used for the analysis is commercially available from Beckman Coulter and is known as the "ANNEXIN V-FITC Kit." The mixture was incubated on ice for 10 minutes. The fluorescent emissions of FITC and PI were detected by flow cytometry (Beckman Coulter) with the excitation filters of 492 nanometers (nm) and 550 nm. The FITC fluorescent emissions signals the presence of cells undergoing apoptosis; whereas, the PI signals with an automatic red color fluorescence the binding to DNA fragments identifying cells in a necrotic stage.

Figure 3:
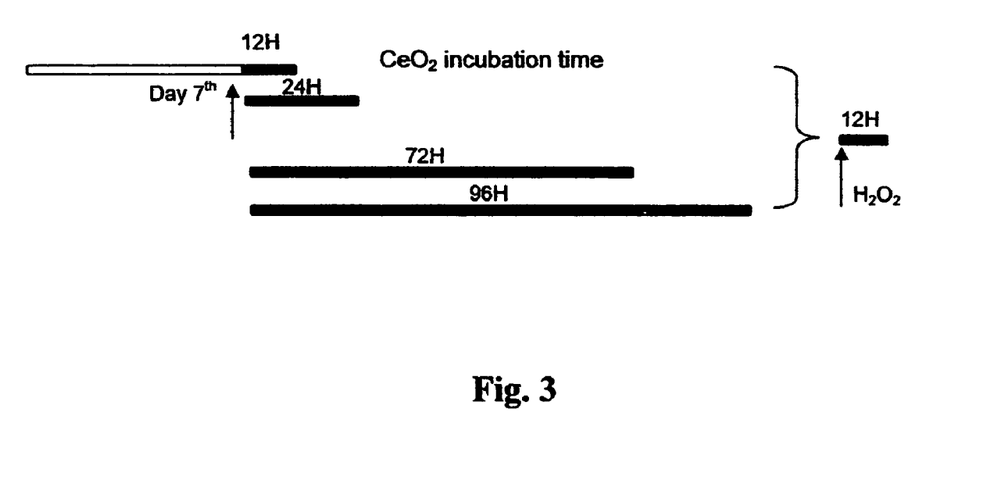
FIG. 3 shows the initial cerium oxide nanoparticle treatments followed by hydrogen peroxide incubation, and time line of exposure.

FIG. 3 shows a treatment timeline with $CeO_2$ incubation after the $7^{th}$ day of treatment at the time intervals of 12 hours, 24 hours, 72 hours and 96 hours with each treated sample subsequently exposed to 12 hours incubation time with $H_2O_2$.

FIGS. 4A-4H are representative flow cytometry plots of retinal neurons with and without incubation with $CeO_2$ nanoparticles. Measurements were taken after 96 hours. The cytometry plot shows activity of approximately 10,000 cells in four quadrants, as described below.

C1 represents the percentage of 10,000 cells showing Annexin V positive signals, which are interpreted to indicate the percentage of 10,000 cells undergoing apoptosis.

C2 represents the percentage of 10,000 cells showing both Annexin V and PI positive signals, which is interpreted as the percentage of 10,000 cells which are in late apoptotic or necrotic stage. (AnnexinV signals apoptotic stage; PI signals necrotic stage.)

C3 represents the percentage of 10,000 cells showing neither Annexin V nor PI positive signals, which is interpreted as the percentage of 10,000 cells which are still viable.

C4 represents the percentage of 10,000 cells showing a PI positive signal, which is interpreted as the percentage of 10,000 cells in a necrotic stage.

Quadrants C2 and C4 show the percentage of 10,000 cells committed to die. In quadrant C1 the percentage of 10,000 cells undergoing apoptosis are shown and some may be salvaged. It is important to observe the percentage of 10,000 cells in quadrant C2 for the efficacy of the cerium oxide treatment of the present invention.

Figure 4A:
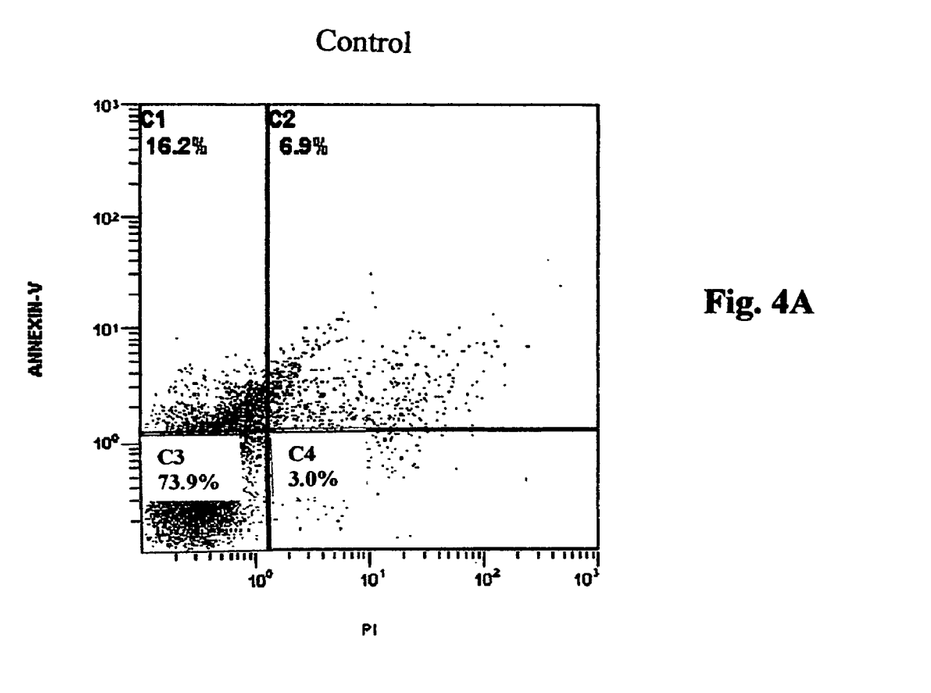
FIG. 4A is a flow cytometry plot of the control sample of primary retinal neurons with no cerium oxide nanoparticle treatments and no hydrogen peroxide incubation.
Figure 4B:
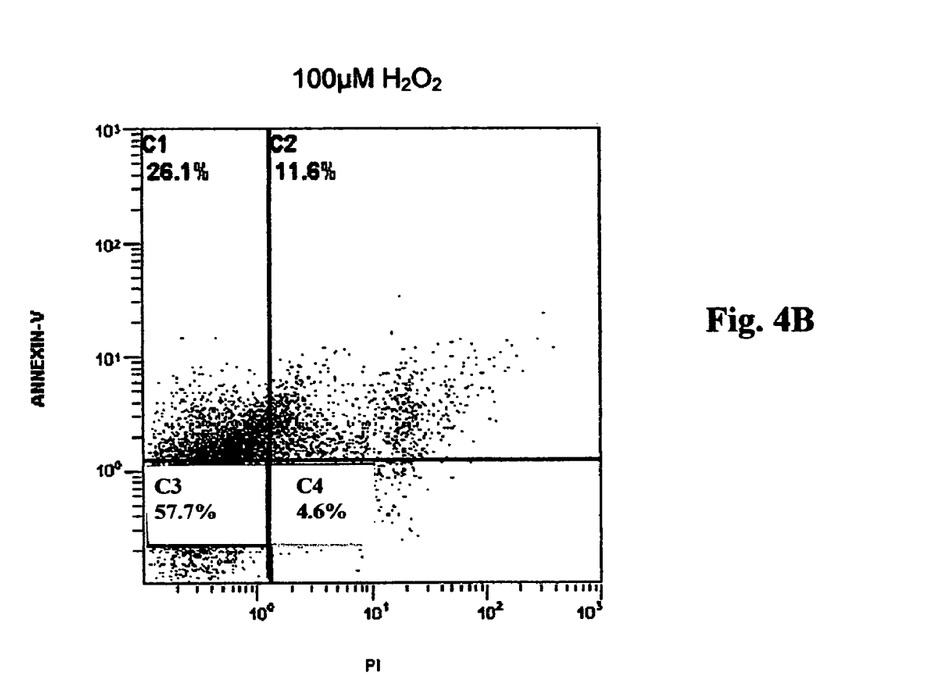
FIG. 4B is a flow cytometry plot of retinal neurons in the presence of 100 micromoles (μM) hydrogen peroxide.

Focusing on the viable cells, the control in FIG. 4A has no $CeO_2$ nanoparticle treatment and 73.9% of the cell population is viable after 96 hours. FIG. 4B is treated with 100 μM $H_2O_2$, causing a deadly assault and leaving the lowest percentage (57.7%) of viable cells. The addition of gradually increasing concentrations of cerium oxide with 100 μM $H_2O_2$, are shown in FIGS. 4C-4G.

Figure 4C:
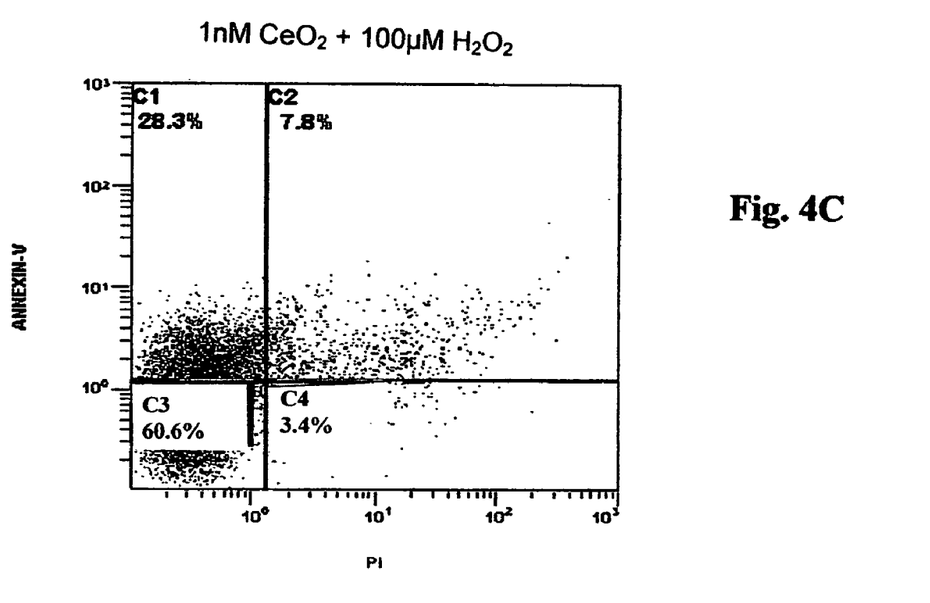
FIG. 4C is a flow cytometry plot of retinal neurons treated with 1 nM cerium oxide in the presence of 100 micromoles (μM) hydrogen peroxide.
Figure 4D:
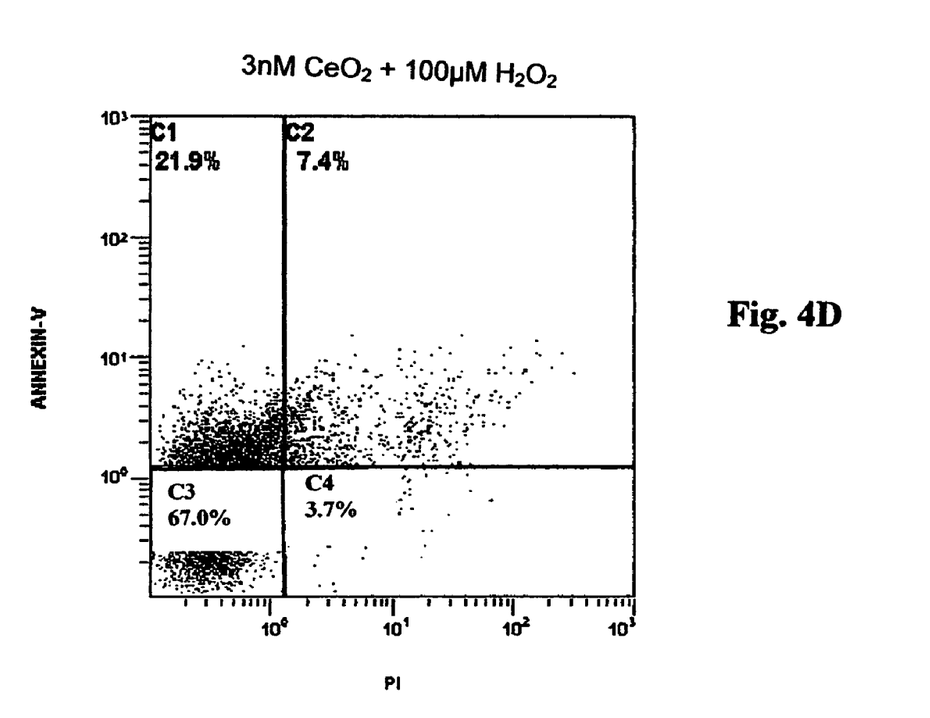
FIG. 4D is a flow cytometry plot of retinal neurons treated with 3 nM cerium oxide in the presence of 100 micromoles (μM) hydrogen peroxide.
Figure 4E:
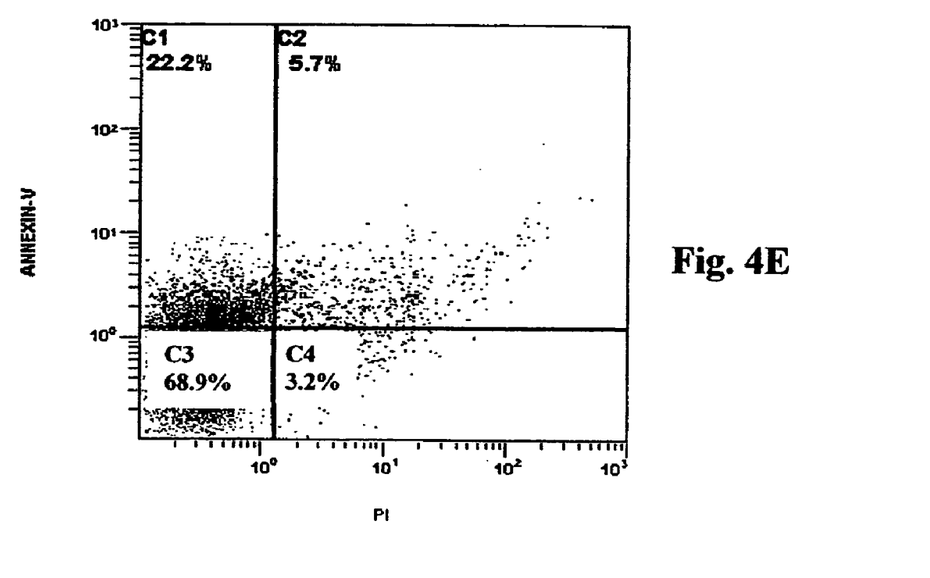
FIG. 4E is a flow cytometry plot of retinal neurons treated with 5 nM cerium oxide in the presence of 100 micromoles (μM) hydrogen peroxide.
Figure 4F:
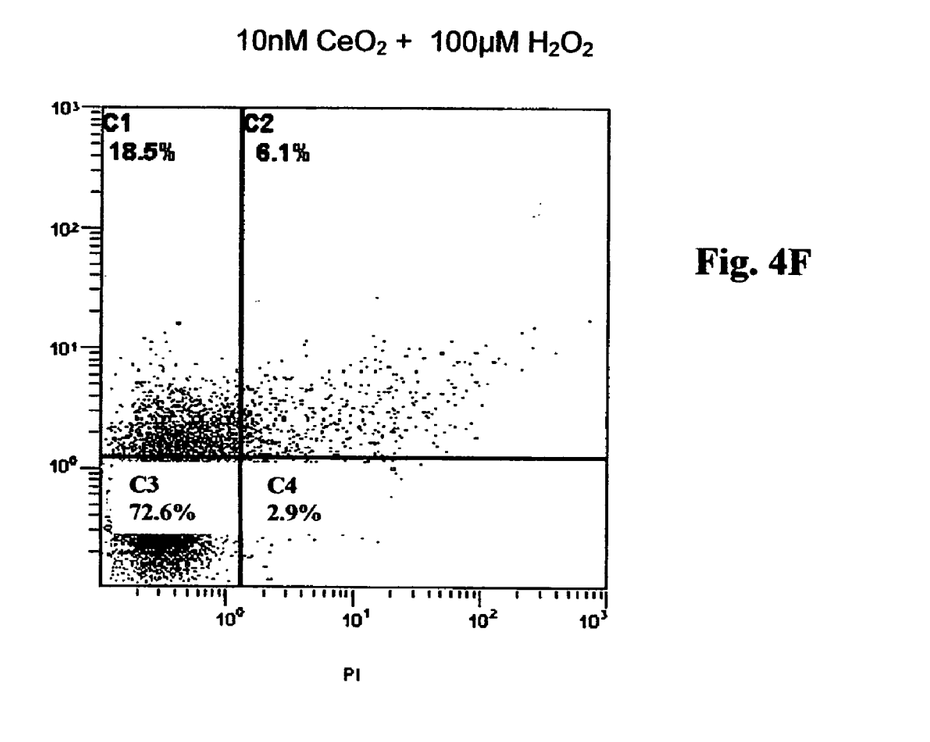
FIG. 4F is a flow cytometry plot of retinal neurons treated with 10 nM cerium oxide in the presence of 100 micromoles (μM) hydrogen peroxide.
Figure 4G:
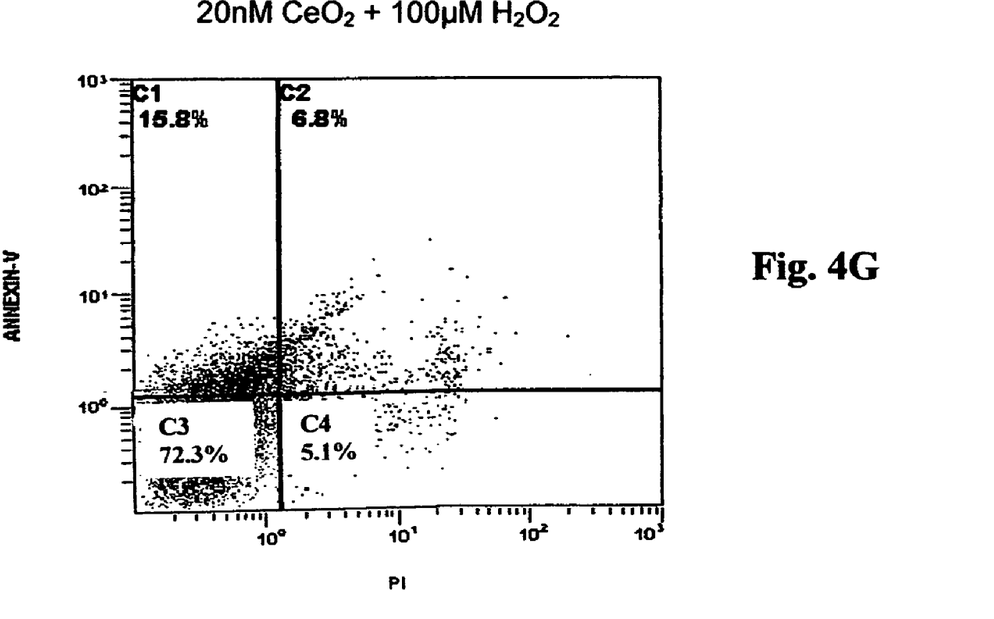
FIG. 4G is a flow cytometry plot of retinal neurons treated with 20 nM cerium oxide in the presence of 100 micromoles (μM) hydrogen peroxide.

FIG. 4C is treated with 1 nM $CeO_2$ nanoparticles and 100 μM $H_2O_2$ and 60.6% of the cell population remains viable. FIG. 4D is treated with 3 nM $CeO_2$ nanoparticles and 100 μM $H_2O_2$ and 67.0% of the cell population is viable. FIG. 4E is treated with 5 nM $CeO_2$ nanoparticles and 100 μM $H_2O_2$, with 68.9% of the cell population remaining viable. FIG. 4F is treated with 10 nM $CeO_2$ nanoparticles and 100 μM $H_2O_2$ and 72.6% of the cell population is viable. FIG. 4G is treated with 20 nM $CeO_2$ nanoparticles and 100 μM $H_2O_2$ and 72.3% of the cell population remains viable.

Figure 4H:
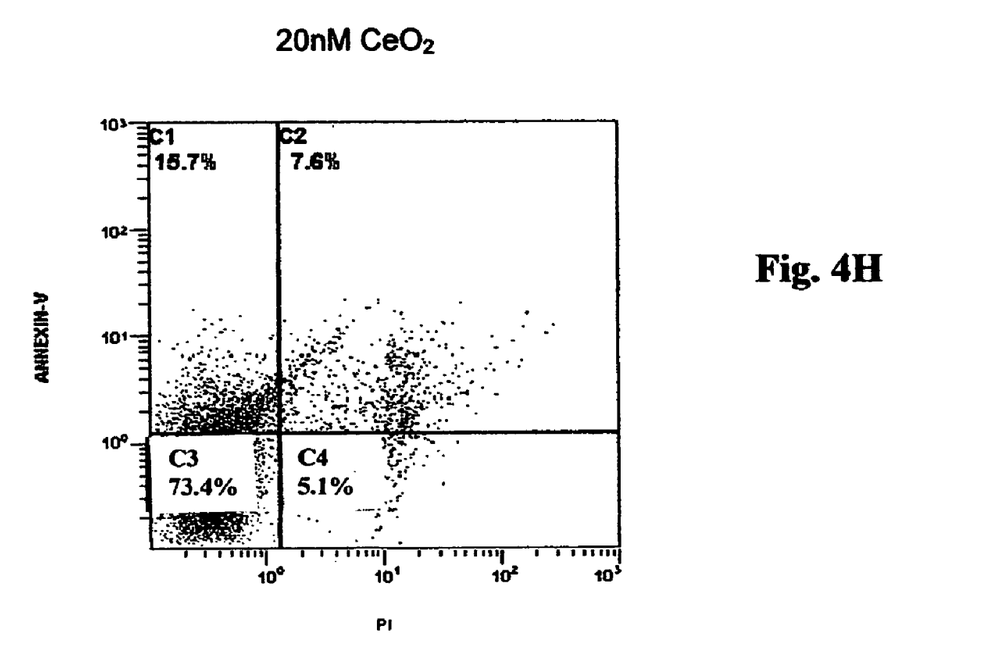
FIG. 4H is a flow cytometry plot of retinal neurons treated with 20 nM cerium oxide.

FIG. 4H is treated with 20 nM $CeO_2$ nanoparticles without the addition of $H_2O_2$ and 73.4% of the cell population remains viable showing that the $CeO_2$ nanoparticles alone have no negative effect on the cell population.

The data in FIGS. 4A-4H can also be summarized from the analysis of cells undergoing apoptosis as shown in quadrant C1. The control, FIG. 4A shows 16.2% of cells undergoing apoptosis under normal conditions, without any treatment, after 96 hours. FIG. 4B shows 26.1% of cells undergoing apoptosis after the 100 μM $H_2O_2$ challenge. FIGS. 4C-4G show there are 28.3%, 21.9%, 22.2%, 18.5% and 15.8% of cells undergoing apoptosis with 1, 3, 5, 10 and 20 nM $CeO_2$ nanoparticle treatment, respectively. FIG. 4H shows 15.7% of cells undergoing apoptosis with 20 nM $CeO_2$ nanoparticle treatment, which is a slight improvement over no treatment at all as shown by the control in FIG. 4A.

Thus, cerium oxide nanoparticles inhibit apoptosis in retinal neurons in vitro in a dose and time dependent manner.

Figure 5:
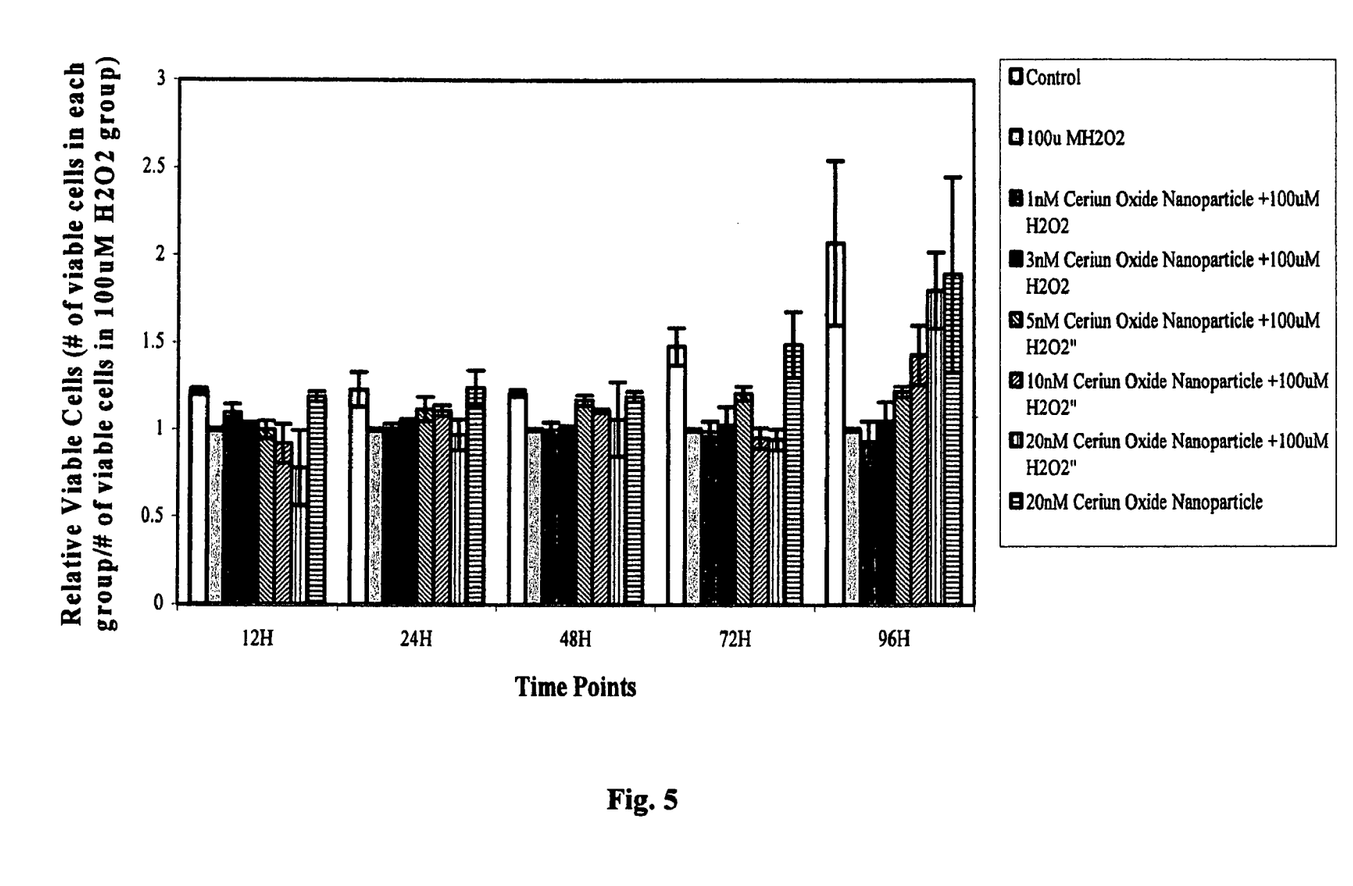
FIG. 5 shows relative viable retinal neurons with and without incubation of different concentrations of cerium oxide nanoparticles for time periods between approximately 12 hours and approximately 96 hours.

FIG. 5 shows relative viable retinal neurons with and without incubation of different concentration of $CeO_2$ nanoparticles for different time periods. The concentration of $CeO_2$ nanoparticles were 1 nM, 3 nM, 5 nM, 10 nM, 20 nM each with 100 μM $H_2O_2$; one sample was treated with only 100 μM $H_2O_2$ and another sample was treated with only 20 nM $CeO_2$ nanoparticles. The measurement of relative viable cells for each group was determined after 12 hours, 24 hours, 48 hours, 72 hours and 96 hours. The effects showed dose and time dependency.

5 nM cerium oxide nanoparticles started to decrease the apoptosis at 24 h of incubation. As incubation time increased, the protective effect from 5 nM nanoparticles was more significantly increased. Additionally, 10 nM and 20 nM nanoparticles began to have effects late with 96 h of incubation. (Statistical analysis was done by ANOVA, and Duncan test for post hoc analysis. Data are presented in M±S.D. n≥3, *p<0.05, **p<0.01). FIG. 5 shows that among the various treatment doses, 5 nM $CeO_2$ nanoparticle treatment gave the earliest response with moderate protective effect and 20 nM $CeO_2$ nanoparticle treatment gave the highest protective effect with late response.

EXAMPLE 3

Intracellular reactive oxygen species (ROS) production was measured in both $CeO_2$ nanoparticle treated and control cells using 29,79-dichlorofluorescein diacetate (DCFH-DA, Sigma). Briefly, the retinal neurons were exposed to $CeO_2$ nanoparticles with different concentrations and various incubation times. After incubation, the cells were incubated with 10 μM DCFH-DA (dissolved in dimethylsulfoxide (DMSO)) at 37° C. for 30 min. The cells then were incubated with 1 mM $H_2O_2$ at 37° C. for 30 min after the excess DCFH-DA was washed with PBS. The cells were harvested as described above. The intensity of fluorescence was detected by flow cytometry with the excitation filter of 485 nm. The ROS level was calculated as a ratio: ROS=mean intensity of treated cells divided by mean intensity of control cells.

Figure 6:
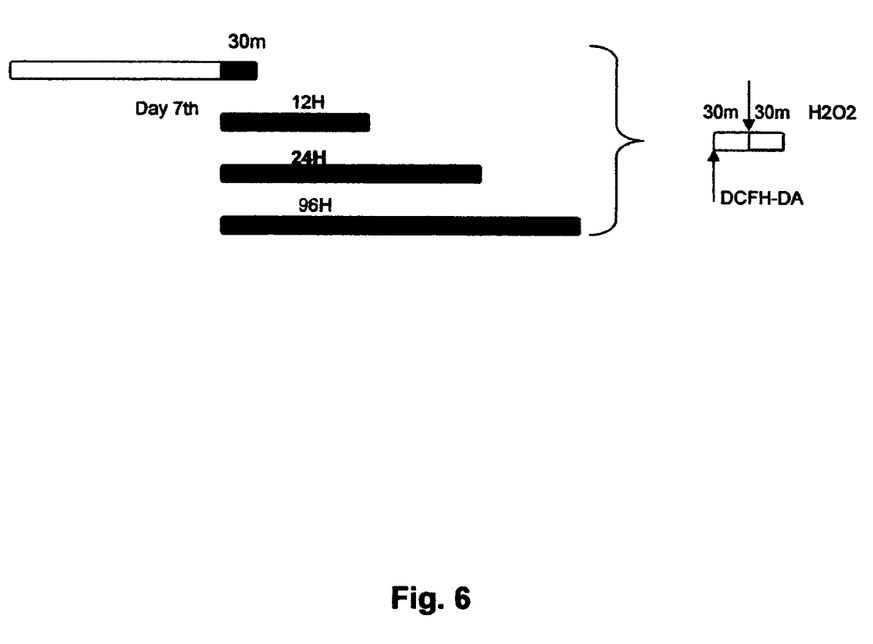
FIG. 6 shows the initial cerium oxide nanoparticle treatments, hydrogen peroxide and DCFH-DA incubation, and time line of exposure.
Figure 7A:
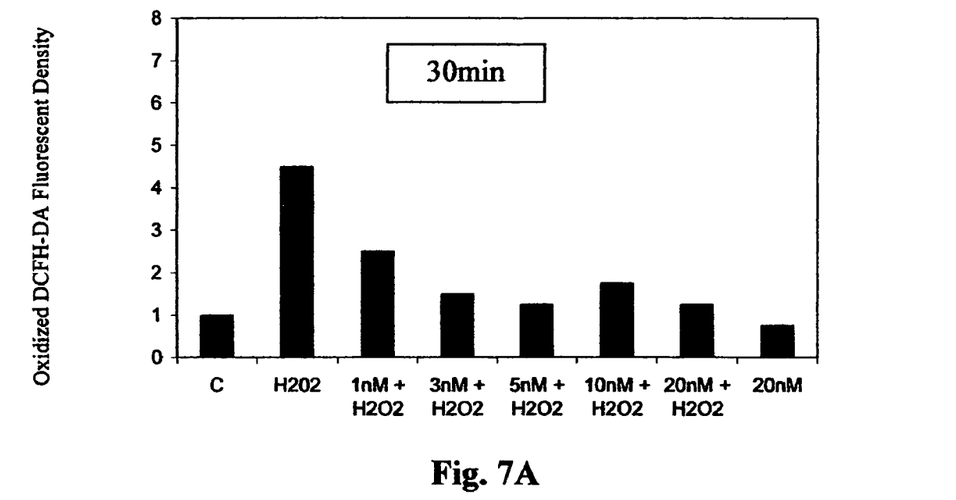
FIG. 7A is a graph of the intracellular level of reactive oxygen species (ROS) of retinal neurons after 30 minutes incubation with cerium oxide nanoparticles.
Figure 7B:
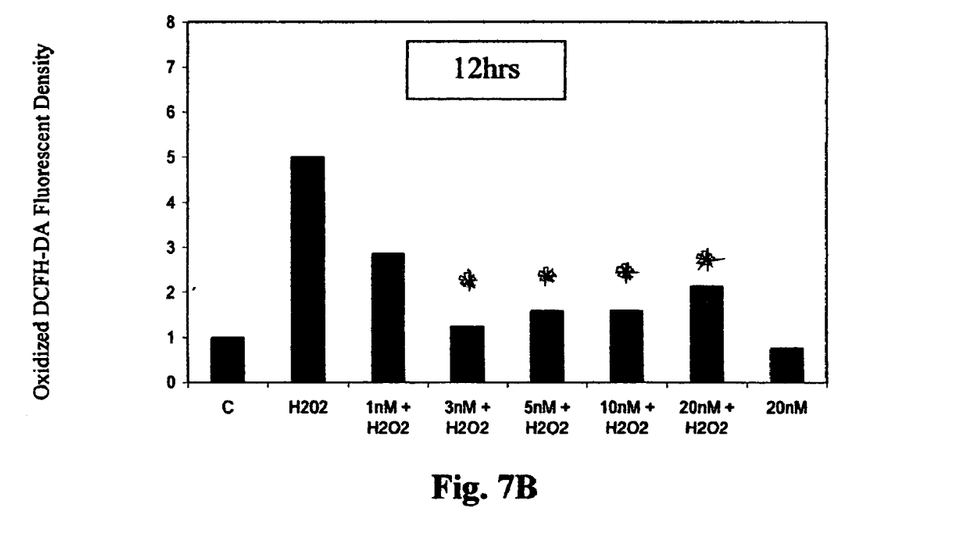
FIG. 7B is a graph of the intracellular level of reactive oxygen species (ROS) of retinal neurons after 12 hours incubation with cerium oxide nanoparticles.
Figure 7C:
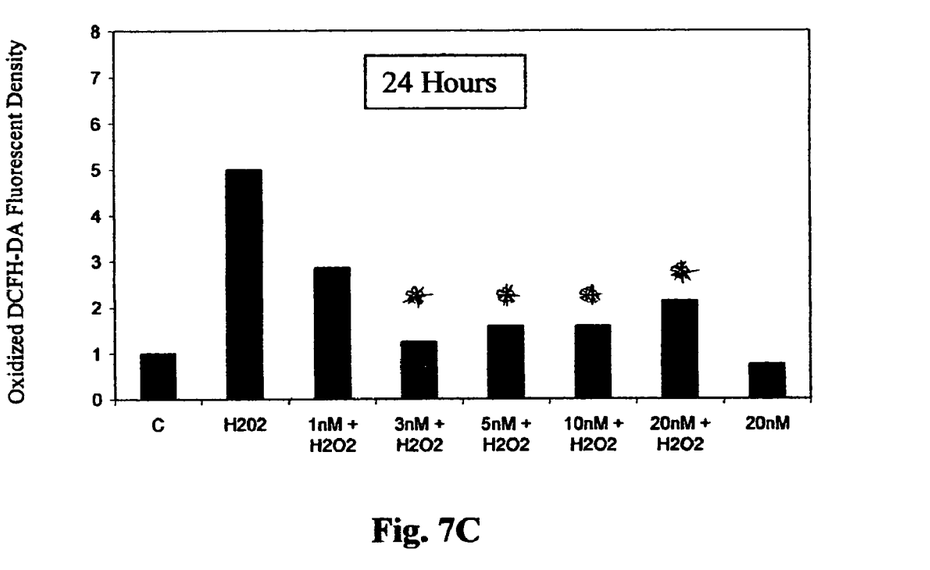
FIG. 7C is a graph of the intracellular level of reactive oxygen species (ROS) of retinal neurons after 24 hours incubation with cerium oxide nanoparticles.
Figure 7D:
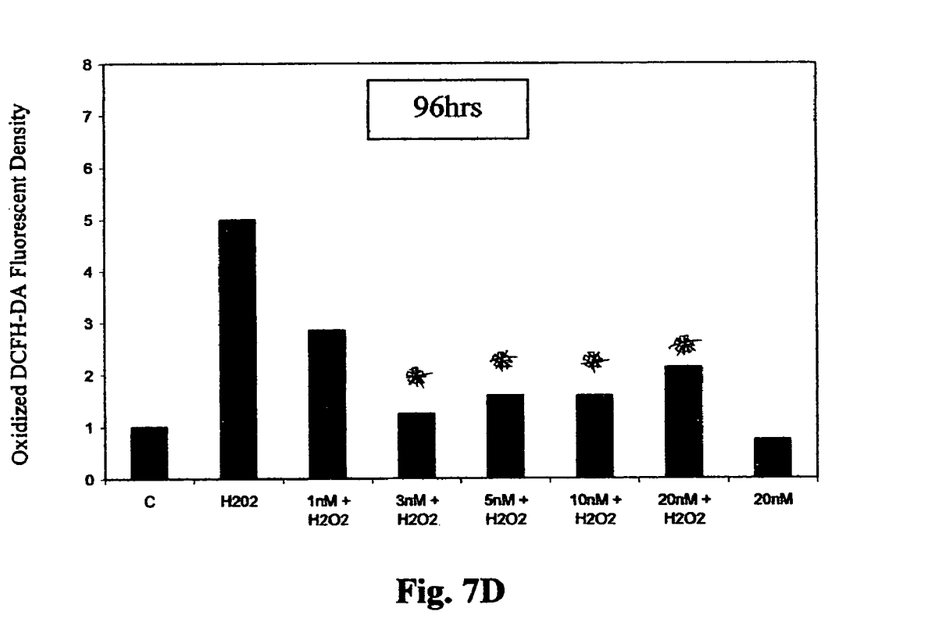
FIG. 7D is a graph of the intracellular level of reactive oxygen species (ROS) of retinal neurons after 96 hours incubation with cerium oxide nanoparticles.

FIG. 6 is an experimental paradigm showing the beginning of the $CeO_2$ nanoparticle treatment on the $7^{th}$ day and simultaneous incubation with $H_2O_2$ and DCFH-DA and a timeline of exposure at 30 minutes, 12 hours, 24 hours, and 96 hours. FIGS. 7A-7D show how the $CeO_2$ nanoparticles decreased the generation of ROS in a dose and time dependent manner. The ROS generated in the groups of 5 nM, 10 nM, and 20 nM nanoparticle incubation were statistically significantly less than the group without treatment at the earliest (12 h) of the tested points. 3 nM nanoparticle incubation had an effect at 24 h. However, 1 nM nanoparticles did not show any significant decrease within the tested time point. Statistical analysis was done by ANOVA, and Duncan test for post hoc analysis. Data were shown in M±S.D. n=3, **$p<0.01$; *$p<0.05$.

The cerium oxide of the present invention includes those cerium compounds that have reacted with atmospheric oxygen to have stable oxide layers identified as $CeO_{n1}$, wherein 0 is less than 1 or equal to 2 ($0<n1<2$) and ($0<n2<3$).

The cerium oxide particles of the present invention are characterized as ultra-fine and are preferably in a size range of from approximately 1 nanometer in diameter to approximately 10 nanometers in diameter; more preferably from approximately 1 nm to approximately 7 nm. A judicious selection of particle size is required by someone skilled in the art and is not a limitation of the present invention.

The results of testing in the above examples document the ability of cerium oxide nanoparticles to promote the longevity of retinal neurons in vitro and inhibit apoptosis induced by hydrogen peroxide on retinal neurons in vitro in a dose and time dependent manner. It has also been determined that cerium oxide nanoparticles decrease generation of intracellular reactive oxygen species in a dose and time dependent manner. Thus, the present invention represents a significant advance in the treatment in degenerative diseases of the retina, such as, but not limited to light-induced retina degeneration and age-related macular degeneration (AMD).

In the second embodiment of the present invention a rat "light damage" model for retinal degeneration was used as the test system. The data demonstrate that the nanoceria prevented the death of retinal neurons when given prior to the "light insult". The nanoceria particles protected the cells at the time of exposure as well as prevented the subsequent death seen days later in the untreated animals. The in vivo route of administration, including, direct injection into the eye, intravenous, intraperitoneal, intramuscular, oral or topically on the eye or skin may improve the result. Similarly, the time of administration of the nanoparticle, both before or after an insult, is important. Thus, the nanoceria will also prevent the death of retinal cells due to glaucoma, diabetic retinopathy, inherited retinal degeneration (for example, Retinitis Pigmentosa), macular degeneration, retinal detachment or any disease or event which proceeds through the production of ROS. These particles should preserve and prolong vision when administered in vivo.

EXAMPLE 4

Rats were injected intravitreally with 2 microliters (μl) of nanoceria (concentrations from 0.1 to 1.0 micromolar) three days before they were exposed for six hours to a bright light (2700 LUX) in a light box. The animals were returned to normal lighting for 3.5 days, then killed, the eyes enucleated, fixed, processed for paraffin embedding, sectioned, and either stained with H & E or processed for immunocytochemistry.

The number of photoreceptors remaining was determined with the H&E sections by using a microscope connected to a digital camera to record the images and then measuring the thickness of the outer nuclear layer every 240 microns from the optic nerve along both the superior and the inferior retina to the ora seratta. The data was then plotted as retina thickness versus the distance from the optic nerve head. The changes in other layers of retinal cells were recorded with images but not quantified. Cells actively undergoing apoptosis were also visualized using a commercially available "Apoptosis kit" and recording the microscopic images with a fluorescence microscope.

The data demonstrate that the nanoceria at all concentrations tested prevented the immediate death of retinal cells shortly after exposure to light as well as the ongoing death seen days later in the untreated animals. We therefore have demonstrated in vivo that these nanoceria particles can protect cells within the rat retina from light-induced cell death.

Prior to the present invention, it was not known that nanoceria particles could be used in vivo for preventing blindness or death of retinal cells, or for preventing the death in vivo of any other cell type in any disease. The chemical properties of CeO2 nanoparticles enable the destruction of reactive oxygen species (ROS) produced by toxins and/or products of oxygen metabolism within cells.

Thus, nanoceria can protect any cell type from ROS induced damages. Diseases which could possibly be prevented, cured or ameliorated would include hereditary blindness, macular degeneration, glaucoma, diabetic retinopathy, retinal detachment, and other blinding diseases which involve ROS would be potentially solved. Similarly, in other cells within the central nervous system (CNS), neuronal death in strokes, degenerative diseases such as Alzheimer's Disease, Parkinson's, Huntington's Disease, and the death of peripheral nerves are preventable or at least the rate of cell death can be decreased and would result in prolonged function of the cells, tissues, organs, and individual.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A composition of matter consisting essentially of a plurality of nanoceria particles in contact with isolated retinal neurons wherein the plurality of nanoceria particles comprises at least one of $CeO_2$ and $Ce_2O_3$ in the form of a plurality of ultra-fine particles, wherein each particle has a diameter in a range between approximately 1 nanometer (nm) and approximately 10 nm, and the combination of the plurality of nanoceria particles in contact with isolated retinal neurons inhibits apoptosis of the isolated retinal neurons in a dose and time dependent manner.

2. The plurality of nanoceria particles in contact with isolated retinal neurons of claim 1, wherein the dosage amount is selected from at least one of 3 (nanomole) nM, 5 nM, 10 nM, and 20 nM of nanoceria particles.

* * * * *